US006995111B2

(12) United States Patent
Levin et al.

(10) Patent No.: US 6,995,111 B2
(45) Date of Patent: *Feb. 7, 2006

(54) MOLECULAR SIEVE COMPOSITIONS, CATALYSTS THEREOF, THEIR MAKING AND USE IN CONVERSION PROCESSES

(75) Inventors: Doron Levin, Annadale, NJ (US); James Clark Vartuli, Schwenksville, PA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 234 days.

This patent is subject to a terminal disclaimer.

(21) Appl. No.: 10/364,870

(22) Filed: Feb. 10, 2003

(65) Prior Publication Data

US 2003/0176753 A1 Sep. 18, 2003

Related U.S. Application Data

(63) Continuation-in-part of application No. 10/215,511, filed on Aug. 9, 2002.
(60) Provisional application No. 60/360,963, filed on Feb. 28, 2002, and provisional application No. 60/366,012, filed on Mar. 20, 2002.

(51) Int. Cl.
*B01J 27/182* (2006.01)
*B01J 21/00* (2006.01)

(52) U.S. Cl. .......................... 502/214; 502/208; 502/73
(58) Field of Classification Search .................. 502/73, 502/208, 214
See application file for complete search history.

(56) References Cited

U.S. PATENT DOCUMENTS

| 4,062,905 A | 12/1977 | Chang et al. ............... 260/682 |
|---|---|---|
| 4,079,095 A | 3/1978 | Givens et al. .............. 260/682 |
| 4,310,440 A | 1/1982 | Wilson et al. .............. 252/435 |
| 4,377,294 A | 3/1983 | Lockwood et al. ... 280/154.5 R |
| 4,440,871 A | 4/1984 | Lok et al. ................... 502/214 |
| 4,465,889 A | 8/1984 | Anthony et al. ............ 585/640 |
| 4,471,150 A | 9/1984 | Wu ............................. 585/640 |
| 4,481,376 A | 11/1984 | Wunder et al. ............. 585/640 |
| 4,499,327 A | 2/1985 | Kaiser ......................... 585/640 |
| 4,663,305 A | 5/1987 | Mauldin et al. ............. 502/304 |
| 4,664,780 A | 5/1987 | Lochow et al. ............. 208/120 |
| 4,677,242 A | 6/1987 | Kaiser ......................... 585/638 |
| 4,677,243 A | 6/1987 | Kaiser ......................... 585/638 |
| 4,769,509 A | 9/1988 | Josefowicz ................. 585/500 |
| 4,873,390 A | 10/1989 | Lewis et al. ................ 585/638 |
| 5,047,379 A | 9/1991 | Alyea et al. ................. 502/79 |
| 5,095,163 A | 3/1992 | Barger ........................ 585/640 |
| 5,130,144 A | 7/1992 | Igarashi ...................... 423/652 |
| 5,208,200 A | 5/1993 | Soled et al. ................ 502/241 |
| 5,227,352 A | 7/1993 | Tsujii et al. ................... 502/65 |
| 5,347,056 A | 9/1994 | Watanabe et al. ........... 568/881 |
| 5,367,100 A | 11/1994 | Gongwei et al. ............ 585/640 |
| 5,371,312 A | 12/1994 | Lago et al. .................. 585/475 |
| 5,417,949 A | 5/1995 | McWilliams .............. 423/239.2 |
| 5,430,000 A | 7/1995 | Timken ........................ 502/60 |
| 5,559,275 A | 9/1996 | Barger ........................ 568/905 |
| 5,714,662 A | 2/1998 | Vora et al. .................. 585/640 |
| 5,728,644 A | 3/1998 | Ho et al. .................... 502/322 |
| 5,977,425 A | 11/1999 | Brandes et al. ............. 585/734 |
| 6,046,373 A | 4/2000 | Sun ............................. 585/640 |
| 6,114,268 A | 9/2000 | Wu et al. ...................... 502/74 |
| 6,166,282 A | 12/2000 | Miller ........................ 585/638 |
| 6,180,828 B1 | 1/2001 | Hidaka et al. .............. 564/479 |
| 6,228,799 B1 | 5/2001 | Aubert et al. ............... 502/304 |
| 2001/0002383 A1 | 5/2001 | Hidaka et al. ................ 502/72 |
| 2002/0013505 A1 | 1/2002 | Fung et al. ................. 585/640 |
| 2002/0119887 A1 | 8/2002 | Huo et al. .................... 502/60 |
| 2004/0034178 A1 | 2/2004 | Vaughn et al. ................ 526/90 |

FOREIGN PATENT DOCUMENTS

| EP | 0 208 868 | 5/1985 |
|---|---|---|
| EP | 0 256 875 | 2/1988 |
| EP | 0 312 981 | 4/1989 |
| EP | 0 697 247 | 7/1995 |
| EP | 0 923 512 | 6/1999 |
| EP | 0 967 011 | 12/1999 |
| EP | 0 993 867 | 4/2000 |
| EP | 0 906 244 | 1/2002 |
| FR | 2661171 | 4/1990 |
| JP | 2001028216 | 4/1999 |
| WO | 96/16142 | 5/1996 |
| WO | WO 98/29370 | 9/1998 |
| WO | 99/41334 | 8/1999 |
| WO | WO 01/47810 | 5/2001 |
| WO | 01/64340 | 9/2001 |
| WO | WO 02/05952 | 1/2002 |

OTHER PUBLICATIONS

Jacobs et al., *Properties of Zeolites in Relation to Their Electronegativity: Acidity, Carboniogenic Activity and Strength of Interaction in Transition Metal Complexes*, J. Inorg. Nucl. Chem., vol. 40, pp. 1919–1923, (1978), no month.

Kang et al., *Effects of Decrease in Number of Acid Sites Located on the External Surface of Ni–SAPO–34 Cyrstalline Catalyst by the Mechanochemical Method*, Catalysis Letter, vol. 53, pp. 171–176, (1998), no month.

Mortier et al, Electronegativity Equalization and Solid State Chemistry of Zeolites, Innovation Zeolite Material Sieves, vol. 37, pp. 253–267, (1998), no month.

W. J. Mortier, *Zeolite Electronegativity Related to Physicochemical Properties*, Journal of Catalysis, vol. 55, pp. 138–145, (1978), no month.

Tseng, et al., Isosynthesis Reactions of CO/H2 Over Zirconium Dioxide, Journal of Catalysis, vol. 109, pp. 284–297, (1988), no month.

*Primary Examiner*—Elizabeth D. Wood

(57) ABSTRACT

The invention relates to a catalyst composition, a method of making the same and its use in the conversion of a feedstock, preferably an oxygenated feedstock, into one or more olefin(s), preferably ethylene and/or propylene The catalyst composition comprises a molecular sieve and at least one oxide of a metal selected from Group 3 of the Periodic Table of Elements, the Lanthanide series of elements and the Actinide series of elements.

29 Claims, No Drawings

MOLECULAR SIEVE COMPOSITIONS, CATALYSTS THEREOF, THEIR MAKING AND USE IN CONVERSION PROCESSES

CROSS REFERENCE TO RELATED APPLICATIONS

The present application is a continuation-in-part of U.S. patent application Ser. No. 10/215,511 filed Aug. 9, 2002 and issued as U.S. Pat. No. 6,906,232. The present application also is related to U.S. patent application Ser. No. 60/374,697 filed concurrently herewith, both of which provisional applications have been incorporated into U.S. Pat. No. 6,844,291. The entire contents of all of these patents and applications are incorporated herein by reference.

FIELD

The present invention relates to molecular sieve compositions and catalysts containing the same, to the synthesis of such compositions and catalysts and to the use of such compositions and catalysts in conversion processes to produce olefin(s).

BACKGROUND

Olefins are traditionally produced from petroleum feedstocks by catalytic or steam cracking processes. These cracking processes, especially steam cracking, produce light olefin(s), such as ethylene and/or propylene, from a variety of hydrocarbon feedstocks. Ethylene and propylene are important commodity petrochemicals useful in a variety of processes for making plastics and other chemical compounds.

The petrochemical industry has known for some time that oxygenates, especially alcohols, are convertible into light olefin(s). There are numerous technologies available for producing oxygenates including fermentation or reaction of synthesis gas derived from natural gas, petroleum liquids or carbonaceous materials including coal, recycled plastics, municipal waste or any other organic material. Generally, the production of synthesis gas involves a combustion reaction of natural gas, mostly methane, and an oxygen source into hydrogen, carbon monoxide and/or carbon dioxide. Other known syngas production processes include conventional steam reforming, autothermal reforming, or a combination thereof.

Methanol, the preferred alcohol for light olefin production, is typically synthesized from the catalytic reaction of hydrogen, carbon monoxide and/or carbon dioxide in a methanol reactor in the presence of a heterogeneous catalyst. For example, in one synthesis process methanol is produced using a copper/zinc oxide catalyst in a water-cooled tubular methanol reactor. The preferred process for converting a feedstock containing methanol into one or more olefin(s), primarily ethylene and/or propylene, involves contacting the feedstock with a molecular sieve catalyst composition.

Molecular sieves are porous solids having pores of different sizes such as zeolites or zeolite-type molecular sieves, carbons and oxides. The most commercially useful molecular sieves for the petroleum and petrochemical industries are known as zeolites, for example aluminosilicate molecular sieves. Zeolites in general have a one-, two- or three-dimensional crystalline pore structure having uniformly sized pores of molecular dimensions that selectively adsorb molecules that can enter the pores, and exclude those molecules that are too large.

There are many different types of molecular sieve well known to convert a feedstock, especially an oxygenate containing feedstock, into one or more olefin(s). For example, U.S. Pat. No. 5,367,100 describes the use of the zeolite, ZSM-5, to convert methanol into olefin(s); U.S. Pat. No. 4,062,905 discusses the conversion of methanol and other oxygenates to ethylene and propylene using crystalline aluminosilicate zeolites, for example Zeolite T, ZK5, erionite and chabazite; U.S. Pat. No. 4,079,095 describes the use of ZSM-34 to convert methanol to hydrocarbon products such as ethylene and propylene; and U.S. Pat. No. 4,310,440 describes producing light olefin(s) from an alcohol using a crystalline aluminophosphate, often designated $AlPO_4$.

Some of the most useful molecular sieves for converting methanol to olefin(s) are silicoaluminophosphate molecular sieves. Silicoaluminophosphate (SAPO) molecular sieves contain a three-dimensional microporous crystalline framework structure of $[SiO_4]$, $[AlO_4]$ and $[PO_4]$ corner sharing tetrahedral units. SAPO synthesis is described in U.S. Pat. No. 4,440,871, which is herein fully incorporated by reference. SAPO molecular sieves are generally synthesized by the hydrothermal crystallization of a reaction mixture of silicon-, aluminum- and phosphorus-sources and at least one templating agent. Synthesis of a SAPO molecular sieve, its formulation into a SAPO catalyst, and its use in converting a hydrocarbon feedstock into olefin(s), particularly where the feedstock is methanol, are disclosed in U.S. Pat. Nos. 4,499,327, 4,677,242, 4,677,243, 4,873,390, 5,095,163, 5,714,662and 6,166,282, all of which are herein fully incorporated by reference.

Typically, molecular sieves are formed into molecular sieve catalyst compositions to improve their durability in commercial conversion processes. These molecular sieve catalyst compositions are formed by combining the molecular sieve and a matrix material usually in the presence of a binder. The purpose of the binder is hold the matrix material, often a clay, to the molecular sieve.

Although it is known to use binders and matrix materials to form molecular sieve catalyst compositions useful in converting oxygenates into olefin(s), these binders and matrix materials typically only serve to provide desired physical characteristics to the catalyst composition, and have little to no effect on conversion and selectivity of the molecular sieve. It would therefore be desirable to have an improved molecular sieve catalyst composition having a better conversion rate, improved olefin selectivity and a longer lifetime.

U.S. Pat. No. 4,465,889 describes a catalyst composition comprising a silicalite molecular sieve impregnated with a thorium, zirconium, or titanium metal oxide for use in converting methanol, dimethyl ether, or a mixture thereof into a hydrocarbon product rich in iso-$C_4$ compounds.

U.S. Pat. No. 6,180,828 discusses the use of a modified molecular sieve to produce methylamines from methanol and ammonia, where for example, a silicoaluminophosphate molecular sieve is combined with one or more modifiers, such as a zirconium oxide, a titanium oxide, an yttrium oxide, montmorillonite or kaolinite.

U.S. Pat. No. 5,417,949 relates to a process for converting noxious nitrogen oxides in an oxygen containing effluent into nitrogen and water using a molecular sieve and a metal oxide binder, where the preferred binder is titania and the molecular sieve is an aluminosilicate.

EP-A-312981 discloses a process for cracking vanadium-containing hydrocarbon feed streams using a catalyst composition comprising a physical mixture of a zeolite embedded in an inorganic refractory matrix material and at least one oxide of beryllium, magnesium, calcium, strontium, barium or lanthanum, preferably magnesium oxide, on a silica-containing support material.

Kang and Inui, *Effects of decrease in number of acid sites located on method, the external surface of Ni-SAPO-34 crystalline catalyst by the mechanochemical Catalysis Letters* 53, pages 171–176 (1998) disclose that the shape selectivity can be enhanced and the coke formation mitigated in the conversion of methanol to ethylene over Ni-SAPO-34 by milling the catalyst with MgO, CaO, BaO or $Cs_2O$ on microspherical non-porous silica, with BaO being the most preferred.

International Publication No. WO 98/29370 discloses the conversion of oxygenates to olefins over a small pore non-zeolitic molecular sieve containing a metal selected from the group consisting of a lanthanide, an actinide, scandium, yttrium, a Group 4 metal, a Group 5 metal or combinations thereof.

SUMMARY

In one aspect, the invention resides in a catalyst composition comprising a molecular sieve and at least one oxide of a metal selected from Group 3 of the Periodic Table of Elements, the Lanthanide series of elements and the Actinide series of elements, wherein said metal oxide has an uptake of carbon dioxide at 100° C. of at least 0.03, and typically at least 0.04, $mg/m^2$ of the metal oxide.

The catalyst composition may also include at least one of a binder and a matrix material different from said metal oxide.

In one embodiment, said metal oxide is selected from lanthanum oxide, yttrium oxide, scandium oxide, cerium oxide, praseodymium oxide, neodymium oxide, samarium oxide, thorium oxide and mixtures thereof.

The molecular sieve conveniently comprises a framework including at least two tetrahedral units selected from $[SiO_4]$, $[AlO_4]$ and $[PO_4]$ units, such as a silicoaluminophosphate.

In another aspect, the invention resides in a molecular sieve catalyst composition comprising a Group 3 metal oxide and/or an oxide of the Lanthanide or Actinide series elements, a binder, a matrix material, and a silicoaluminophosphate molecular sieve.

In another aspect, the invention resides in a method for making a catalyst composition, the method comprising physically mixing first particles comprising a molecular sieve with second particles comprising at least one oxide of a metal selected from Group 3 of the Periodic Table of Elements, the Lanthanide series of elements and the Actinide series of elements, wherein said metal oxide has an uptake of carbon dioxide at 100° C. of at least 0.03 $mg/m^2$ of the metal oxide particles.

In one embodiment, the molecular sieve, a binder and a matrix material are made into a formulated molecular sieve catalyst composition that is then contacted, mixed, combined, spray dried, or the like, with an active Group 3 metal oxide and/or an active oxide of a Lanthanide or Actinide series element.

In another aspect, the invention resides in a method of making a catalyst composition, the method comprising the steps of:
(i) synthesizing a molecular sieve from a reaction mixture comprising at least one templating agent and at least two of a silicon source, a phosphorus source and an aluminum source; and (ii) recovering the molecular sieve synthesized in step (i);
(iii) forming a hydrated precursor of an oxide of a metal selected from Group 3 of the Periodic Table of Elements, the Lanthanide series of elements and the Actinide series of elements by precipitation from a solution containing a source of ions of said metal;
(iv) recovering the hydrated precursor formed in step (iii);
(v) calcining the hydrated precursor recovered in step (iv) to form a calcined metal oxide that has an uptake of carbon dioxide at 100° C. of at least 0.03 $mg/m^2$ of the metal oxide; and
(vi) physically mixing the molecular sieve recovered in step (i) and the calcined metal oxide of step (v).

In yet another aspect, the invention is directed to a process for producing olefin(s) by converting a feedstock, such as an oxygenate, conveniently an alcohol, for example methanol, in the presence of any of the above molecular sieve compositions and/or molecular sieve or formulated molecular sieve catalyst compositions.

In yet another aspect, the invention is directed to an integrated process for making one or more olefin(s), the integrated process comprising the steps of:
(a) passing a hydrocarbon feedstock to a syngas production zone to produce a synthesis gas stream;
(b) contacting the synthesis gas stream with a catalyst to form an oxygenated feedstock; and
(c) converting the oxygenated feedstock into the one or more olefin(s) in the presence of a molecular sieve catalyst composition comprising a molecular sieve and at least one oxide of a metal selected Group 3 or the Lanthanide or Actinide series elements of the Periodic Table of Elements.

In one embodiment, the catalyst composition has a Lifetime Enhancement Index (LEI) greater than 1, such as greater than 1.5. LEI is defined herein as the ratio of the lifetime of the catalyst composition to that of the same catalyst composition in the absence of an active metal oxide.

DETAILED DESCRIPTION OF THE EMBODIMENTS

Introduction

The invention is directed to a molecular sieve catalyst composition and to its use in the conversion of hydrocarbon feedstocks, particularly oxygenated feedstocks, into olefin(s). It has been found that combining a molecular sieve with an active metal oxide from Group 3 of the Periodic Table of Elements (using the IUPAC format described in the *CRC Handbook of Chemistry and Physics*, 78th Edition, CRC Press, Boca Raton, Fla. [1997] and/or the Lanthanide or Actinide series elements results in a catalyst composition with an enhanced olefin yield and/or a longer lifetime when used in the conversion of feedstocks, such as oxygenates, more particularly methanol, into olefin(s). In addition, the resultant catalyst composition tends to be more propylene selective and to yield lower amounts of unwanted ethane and propane, together with other undesirable compounds, such as aldehydes and ketones, specifically acetaldehyde.

Molecular Sieves

Molecular sieves have been classified by the Structure Commission of the International Zeolite Association according to the rules of the IUPAC Commission on Zeolite Nomenclature. According to this classification, framework-type zeolite and zeolite-type molecular sieves, for which a structure has been established, are assigned a three letter code and are described in the *Atlas of Zeolite Framework Types*, 5th edition, Elsevier, London, England (2001), which is herein fully incorporated by reference.

Crystalline molecular sieves all have a 3-dimensional, four-connected framework structure of corner-sharing [TO$_4$] tetrahedra, where T is any tetrahedrally coordinated cation. Molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum, et al., *Introduction to Zeolite Science and Practice, Second Completely Revised and Expanded Edition*, Volume 137, pages 1–67, Elsevier Science, B.V., Amsterdam, Netherlands (2001).

Non-limiting examples of molecular sieves are the small pore molecular sieves, AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof; the medium pore molecular sieves, AFO, AEL, EUO, HEU, FER, MEL, MFI, MTW, MTT, TON, and substituted forms thereof; and the large pore molecular sieves, EMT, FAU, and substituted forms thereof. Other molecular sieves include ANA, BEA, CFI, CLO, DON, GIS, LTL, MER, MOR, MWW and SOD. Non-limiting examples of preferred molecular sieves, particularly for converting an oxygenate containing feedstock into olefin(s), include AEL, AFY, AEI, BEA, CHA, EDI, FAU, FER, GIS, LTA, LTL, MER, MFI, MOR, MTT, MWW, TAM and TON. In one preferred embodiment, the molecular sieve of the invention has an AEI topology or a CHA topology, or a combination thereof, most preferably a CHA topology.

The small, medium and large pore molecular sieves have from a 4-ring to a 12-ring or greater framework-type. In a preferred embodiment, the zeolitic molecular sieves have 8-, 10- or 12-ring structures and an average pore size in the range of from about 3 Å to 15 Å. In a more preferred embodiment, the molecular sieves, preferably silicoaluminophosphate molecular sieves, have 8-rings and an average pore size less than about 5 Å, such as in the range of from 3Å to about 5 Å, for example from 3 Å to about 4.5 Å, and particularly from 3.5 Å to about 4.2 Å.

Molecular sieves have a molecular framework of one, preferably two or more corner-sharing [TO$_4$] tetrahedral units, more preferably, two or more [SiO$_4$], [AlO$_4$] and/or [PO$_4$] tetrahedral units, and most preferably [SiO$_4$], [AlO$_4$] and [PO$_4$] tetrahedral units. These silicon, aluminum, and phosphorus based molecular sieves and metal containing derivatives thereof have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (ELAPSO where El is As, Be, B, Cr, Co, Ga, Ge, Fe, Li, Mg, Mn, Ti or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZnAPSO, EP-A-0 161 489 (CoAPSO), EP-A-0 158 976 (ELAPO, where EL is Co, Fe, Mg, Mn, Ti or Zn), U.S. Pat. No. 4,310,440 (AlPO$_4$), EP-A-0 158 350 (SENAPSO), U.S. Pat. No. 4,973,460 (LiAPSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758,419, 4,882,038, 5,434,326 and 5,478,787 (MgAPSO), U.S. Pat. No. 4,554,143 (FeAPO), U.S. Pat. No. 4,894,213 (AsAPSO), U.S. Pat. No. 4,913,888 (AsAPO), U.S. Pat. Nos. 4,686,092, 4,846,956 and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617 and 4,880,520 (TiAPSO), U.S. Pat. Nos. 4,500,651, 4,551,236 and 4,605,492 (TiAPO), U.S. Pat. Nos. 4,824,554, 4,744,970 (CoAPSO), U.S. Pat. No. 4,735,806 (GaAPSO) EP-A-0 293 937 (QAPSO, where Q is framework oxide unit [QO$_2$]), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066and 5,675,050, all of which are herein fully incorporated by reference.

Other molecular sieves include those described in R. Szostak, *Handbook of Molecular Sieves*, Van Nostrand Reinhold, New York, N.Y. (1992), which is herein fully incorporated by reference.

The more preferred molecular sieves include aluminophosphate (AlPO) molecular sieves and silicoaluminophosphate (SAPO) molecular sieves and substituted, preferably metal substituted, AlPO and SAPO molecular sieves. The most preferred molecular sieves are SAPO molecular sieves, and metal substituted SAPO molecular sieves. In an embodiment, the metal is an alkali metal of Group 1 of the Periodic Table of Elements, an alkaline earth metal of Group 2 of the Periodic Table of Elements, a rare earth metal of Group 3 of the Periodic Table of Elements, including the Lanthanides lanthanum, cerium, praseodymium, neodymium, samarium, europium, gadolinium, terbium, dysprosium, holmium, erbium, thulium, ytterbium and lutetium; and scandium or yttrium, a transition metal of Groups 4 to 12 of the Periodic Table of Elements, or mixtures of any of these metal species. In one preferred embodiment, the metal is selected from the group consisting of Co, Cr, Cu, Fe, Ga, Ge, Mg, Mn, Ni, Sn, Ti, Zn and Zr, and mixtures thereof. In another preferred embodiment, these metal atoms discussed above are inserted into the framework of a molecular sieve through a tetrahedral unit, such as [MeO$_2$], and carry a net charge depending on the valence state of the metal substituent. For example, in one embodiment, when the metal substituent has a valence state of +2, +3, +4, +5, or +6, the net charge of the tetrahedral unit is between −2 and +2.

In one embodiment, the molecular sieve, as described in many of the U.S. Patents mentioned above, is represented by the empirical formula, on an anhydrous basis:

$$mR:(M_xAl_yP_z)O_2$$

wherein R represents at least one templating agent, preferably an organic templating agent; m is the number of moles of R per mole of $(M_xAl_yP_z)O_2$ and has a value from 0 to 1, preferably 0 to 0.5, and most preferably from 0 to 0.3; x, y, and z represent the mole fraction of Al, P and M as tetrahedral oxides, where M is a metal selected from one of Groups 1, 2, 3, 4, 5, 6, 7, 8, 9, 10, 11, 12, 13, 14 and Lanthanide's of the Periodic Table of Elements, preferably M is selected from one of the group consisting of Si, Co, Cr, Cu, Fe, Ga, Ge, Mg, Mn, Ni, Sn, Ti, Zn and Zr. In an embodiment, m is greater than or equal to 0.2, and x, y and z are greater than or equal to 0.01. In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

Non-limiting examples of SAPO and AlPO molecular sieves useful herein include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44 (U.S. Pat. No. 6,162,415), SAPO-47, SAPO-56, AlPO-5, AlPO- 11, AlPO-18, AlPO-31, AlPO-34, AlPO-36, AlPO-37, AlPO-46, and metal containing molecular sieves thereof. Of these, particularly useful molecular sieves are one or a combination of SAPO-18, SAPO-34, SAPO-35, SAPO-44, SAPO-56, AlPO-18 and AlPO-34 and metal containing derivatives thereof, such as one or a combination of SAPO-18, SAPO-34, AlPO-34 and AlPO-18, and metal containing derivatives thereof, and especially one or a combination of SAPO-34 and AlPO-18, and metal containing derivatives thereof.

In an embodiment, the molecular sieve is an intergrowth material having two or more distinct crystalline phases within one molecular sieve composition. In particular, intergrowth molecular sieves are described in the U.S. patent application Ser. No. 09/924,016 filed Aug. 7, 2001 and issued as U.S. Pat. No. 6,812,372 and International Publication No. WO 98/15496 published Apr. 16, 1998, both of which are herein fully incorporated by reference. For example, SAPO-18, AlPO-18 and RUW-18 have an AEI framework-type, and SAPO-34 has a CHA framework-type. Thus the molecular sieve used herein may comprise at least one intergrowth phase of AEI and CHA framework-types, especially where the ratio of CHA framework-type to AEI framework-type, as determined by the DIFFaX method disclosed in U.S. patent application Ser. No. 09/924,016 filed Aug. 7, 2001 and issued as U.S. Pat. No. 6,812,372, is greater than 1:1.

Molecular Sieve Synthesis

The synthesis of molecular sieves is described in many of the references discussed above. Generally, molecular sieves are synthesized by the hydrothermal crystallization of one or more of a source of aluminum, a source of phosphorus, a source of silicon and a templating agent, such as a nitrogen containing organic compound. Typically, a combination of sources of silicon, aluminum and phosphorus, optionally with one or more templating agents, is placed in a sealed pressure vessel, optionally lined with an inert plastic such as polytetrafluoroethylene, and heated, under a crystallization pressure and temperature, until a crystalline material is formed, and then recovered by filtration, centrifugation and/or decanting.

Non-limiting examples of silicon sources include silicates, fumed silica, for example, Aerosil-200 available from Degussa Inc., New York, N.Y., and CAB-O-SIL M-5, organosilicon compounds such as tetraalkyl orthosilicates, for example, tetramethyl orthosilicate (TMOS) and tetraethylorthosilicate (TEOS), colloidal silicas or aqueous suspensions thereof, for example Ludox HS-40 sol available from E.I. du Pont de Nemours, Wilmington, Del., silicic acid or any combination thereof.

Non-limiting examples of aluminum sources include aluminum alkoxides, for example aluminum isopropoxide, aluminum phosphate, aluminum hydroxide, sodium aluminate, pseudo-boehmite, gibbsite and aluminum trichloride, or any combination thereof. A convenient source of aluminum is pseudo-boehmite, particularly when producing a silicoaluminophosphate molecular sieve.

Non-limiting examples of phosphorus sources, which may also include aluminum-containing phosphorus compositions, include phosphoric acid, organic phosphates such as triethyl phosphate, and crystalline or amorphous aluminophosphates such as $AlPO_4$, phosphorus salts, or combinations thereof. A convenient source of phosphorus is phosphoric acid, particularly when producing a silicoaluminophosphate.

Templating agents are generally compounds that contain elements of Group 15 of the Periodic Table of Elements, particularly nitrogen, phosphorus, arsenic and antimony. Typical templating agents also contain at least one alkyl or aryl group, such as an alkyl or aryl group having from 1 to 10 carbon atoms, for example from 1 to 8 carbon atoms. Preferred templating agents are often nitrogen-containing compounds, such as amines, quaternary ammonium compounds and combinations thereof. Suitable quaternary ammonium compounds are represented by the general formula $R_4N^+$, where each R is hydrogen or a hydrocarbyl or substituted hydrocarbyl group, preferably an alkyl group or an aryl group having from 1 to 10 carbon atoms.

Non-limiting examples of templating agents include tetraalkyl ammonium compounds including salts thereof, such as tetramethyl ammonium compounds, tetraethyl ammonium compounds, tetrapropyl ammonium compounds, and tetrabutylammonium compounds, cyclohexylamine, morpholine, di-n-propylamine (DPA), tripropylamine, triethylamine (TEA), triethanolamine, piperidine, cyclohexylamine, 2-methylpyridine, N,N-dimethylbenzylamine, N,N-diethylethanolamine, dicyclohexylamine, N,N-dimethylethanolamine, choline, N,N'-dimethylpiperazine, 1,4-diazabicyclo(2,2,2)octane, N', N',N,N-tetramethyl-(1,6)hexanediamine, N-methyldiethanolamine, N-methyl-ethanolamine, N-methyl piperidine, 3-methyl-piperidine, N-methylcyclohexylamine, 3-methylpyridine, 4-methylpyridine, quinuclidine, N,N'-dimethyl-1,4-diazabicyclo(2,2, 2) octane ion; di-n-butylamine, neopentylamine, di-n-pentylamine, isopropylamine, t-butylamine, ethylenediamine, pyrrolidine, and 2-imidazolidone.

The pH of the synthesis mixture containing at a minimum a silicon-, aluminum-, and/or phosphorus-composition, and a templating agent, is generally in the range of from 2 to 10, such as from 4 to 9, for example from 5 to 8.

Generally, the synthesis mixture described above is sealed in a vessel and heated, preferably under autogenous pressure, to a temperature in the range of from about 80° C. to about 250° C., such as from about 100° C. to about 250° C., for example from about 125° C. to about 225° C., such as from about 150° C. to about 180° C.

In one embodiment, the synthesis of a molecular sieve is aided by seeds from another or the same framework type molecular sieve.

The time required to form the crystalline product is usually dependent on the temperature and can vary from immediately up to several weeks. Typically the crystallization time is from about 30 minutes to around 2 weeks, such as from about 45 minutes to about 240 hours, for example from about 1 hour to about 120 hours. The hydrothermal crystallization may be carried out with or without agitation or stirring.

Once the crystalline molecular sieve product is formed, usually in a slurry state, it may be recovered by any standard technique well known in the art, for example, by centrifugation or filtration. The recovered crystalline product may then be washed, such as with water, and then dried, such as in air.

One method for crystallization involves producing an aqueous reaction mixture containing an excess amount of a templating agent, subjecting the mixture to crystallization under hydrothermal conditions, establishing an equilibrium between molecular sieve formation and dissolution, and then, removing some of the excess templating agent and/or organic base to inhibit dissolution of the molecular sieve. See for example U.S. Pat. No. 5,296,208, which is herein fully incorporated by reference.

Other methods for synthesizing molecular sieves or modifying molecular sieves are described in U.S. Pat. No. 5,879, 655 (controlling the ratio of the templating agent to phosphorus), U.S. Pat. No. 6,005,155 (use of a modifier without a salt), U.S. Pat. No. 5,475,182 (acid extraction), U.S. Pat. No. 5,962,762 (treatment with transition metal), U.S. Pat. Nos. 5,925,586 and 6,153,552 (phosphorus modified), U.S. Pat. No. 5,925,800 (monolith supported), U.S. Pat. No. 5,932,512 (fluorine treated), U.S. Pat. No. 6,046,373 (electromagnetic wave treated or modified), U.S. Pat. No. 6,051,746 (polynuclear aromatic modifier), U.S. Pat. No. 6,225,254 (heating template), PCT WO 01/36329 published May 25, 2001 (surfactant synthesis), PCT WO 01/25151 published Apr. 12, 2001 (staged acid addition), PCT WO 01/60746 published Aug. 23, 2001 (silicon oil), U.S. patent application Ser. No. 09/929,949 filed Aug. 15, 2001 (cooling molecular sieve), now U.S. Pat. No. 6,503,863, U.S. patent application Ser. No. 09/615,526 filed Jul. 13, 2000 (metal impregnation including copper), now U.S. Pat. No. 6,448,197; U.S. patent application Ser. No. 09/672,469 filed Sep. 28, 2000 (conductive microfilter), now U.S. Pat. No. 6,521,562; and U.S. patent application Ser. No. 09/754,812 filed Jan. 4, 2001 (freeze drying the molecular sieve), now U.S. Pat. No. 6,537,941; which are all herein fully incorporated by reference.

Where a templating agent is used in the synthesis of the molecular sieve, any templating agent retained in the product may be removed after crystallization by numerous well known techniques, for example, by calcination. Calcination involves contacting the molecular sieve containing the templating agent with a gas, preferably containing oxygen, at any desired concentration at an elevated temperature sufficient to either partially or completely remove the templating agent.

Aluminosilicate and silicoaluminophosphate molecular sieves have either a high silicon (Si) to aluminum (Al) ratio or a low silicon to aluminum ratio, however, a low Si/Al ratio is preferred for SAPO synthesis. In one embodiment, the molecular sieve has a Si/Al ratio less than 0.65, such as less than 0.40, for example less than 0.32, and particularly less than 0.20. In another embodiment the molecular sieve has a Si/Al ratio in the range of from about 0.65 to about 0.10, such as from about 0.40 to about 0.10, for example from about 0.32 to about 0.10, and particularly from about 0.32 to about 0.15.

Group 3 Metal Oxides and Oxides of the Lanthanide or Actinide Series

The metal oxides useful herein are oxides of Group 3 metals and the Lanthanide and Actinide series metals which have an uptake of carbon dioxide at 100° C. of at least 0.03 mg/m$^2$ of the metal oxide, such as at least 0.04 mg/m$^2$ of the metal oxide. Although the upper limit on the carbon dioxide uptake of the metal oxide is not critical, in general the metal oxides useful herein will have a carbon dioxide at 100° C. of less than 10 mg/m$^2$ of the metal oxide, such as less than 5 mg/m$^2$ of the metal oxide. Typically, the metal oxides useful herein have a carbon dioxide uptake of 0.05 to 1 mg/m$^2$ of the metal oxide. When used in combination with a molecular sieve, such active metal oxides provide benefits in catalytic conversion processes, particularly the conversion of oxygenates to olefins.

In order to determine the carbon dioxide uptake of a metal oxide, the following procedure is adopted. A sample of the metal oxide is dehydrated by heating the sample to about 200° C. to 500° C. in flowing air until a constant weight, the "dry weight", is obtained. The temperature of the sample is then reduced to 100° C. and carbon dioxide is passed over the sample, either continuously or in pulses, again until constant weight is obtained. The increase in weight of the sample in terms of mg/mg of the sample based on the dry weight of the sample is the amount of adsorbed carbon dioxide.

In the Examples reported below, the carbon dioxide adsorption is measured using a Mettler TGA/SDTA 851 thermogravimetric analysis system under ambient pressure. The metal oxide sample is dehydrated in flowing air to about 500° C. for one hour. The temperature of the sample is then reduced in flowing helium to the desired adsorption temperature of 100° C. After the sample has equilibrated at 100° C. in flowing helium, the sample is subjected to 20 separate pulses (about 12 seconds/pulse) of a gaseous mixture comprising 10 weight % carbon dioxide with the remainder being helium. After each pulse of the adsorbing gas the metal oxide sample is flushed with flowing helium for 3 minutes. The increase in weight of the sample in terms of mg/mg adsorbent based on the adsorbent weight after treatment at 500° C. is the amount of adsorbed carbon dioxide. The surface area of the sample is measured in accordance with the method of Brunauer, Emmett, and Teller (BET) published as ASTM D 3663 to provide the carbon dioxide uptake in terms of mg carbon dioxide/m$^2$ of the metal oxide.

Preferred Group 3 metal oxides include oxides of scandium, yttrium and lanthanum, and preferred oxides of the Lanthanide or Actinide series metals include oxides of cerium, praseodymium, neodymium, samarium, europium, gadolinium, terbium, dysprosium, holmium, erbium, thulium, ytterbium, lutetium and thorium. The most preferred active metal oxides are scandium oxide, lanthanum oxide, yttrium oxide, cerium oxide, praseodymium oxide, neodymium oxide and mixtures thereof, particularly mixtures of lanthanum oxide and cerium oxide.

In one embodiment, useful metal oxides are those oxides of Group 3 metals and/or the Lanthanide and Actinide series metals that, when used in combination with a molecular sieve in a catalyst composition, are effective in extending of the useful life of the catalyst composition. Quantification of the extension in the catalyst composition life is determined by the Lifetime Enhancement Index (LEI) as defined by the following equation:

$$LEI = \frac{\text{Lifetime of Catalyst in Combination with Active Metal Oxide(s)}}{\text{Lifetime of Catalyst}} \text{ where}$$

the lifetime of the catalyst or catalyst composition, is measured in the same process under the same conditions, and is the cumulative amount of feedstock processed per gram of catalyst composition until the conversion of feedstock by the catalyst composition falls below some defined level, for example 10%. An inactive metal oxide will have little to no effect on the lifetime of the catalyst composition, or will shorten the lifetime of the catalyst composition, and will therefore have a LEI less than or equal to 1. Active metal oxides of the invention are those Group 3 metal oxides, including oxides of the Lanthanide and Actinide series, that when used in combination with a molecular sieve, provide a molecular sieve catalyst composition that has a LEI greater than 1. By definition, a molecular sieve catalyst composition that has not been combined with an active metal oxide will have a LEI equal to 1.0.

It is found that, by including an active Group 3 metal oxide and/or the active oxide of the Lanthanide or Actinide series in combination with a molecular sieve, a catalyst composition can be produced having an LEI in the range of from greater than 1 to 50, such as from about 1.5 to about 20. Typically catalyst compositions according to the invention exhibit LEI values greater than 1.1, for example in the range of from about 1.2 to 15, and more particularly greater than 1.3, such as greater than 1.5, such as greater than 1.7, such as greater than 2.

In one embodiment, the active Group 3 metal oxide and/or the active oxide of the Lanthanide or Actinide series when combined with a molecular sieve in a catalyst composition enhances the lifetime of the catalyst composition in the conversion of a feedstock comprising methanol, preferably into one or more olefin(s).

The active metal oxide(s) used herein can be prepared using a variety of methods. It is preferable that the active metal oxide is made from an active metal oxide precursor, such as a metal salt, such as a nitrate, halide, sulfate or acetate. Other suitable sources of the metal oxide include compounds that form the metal oxide during calcination, such as oxychlorides and nitrates. Alkoxides are also suitable sources of the Group 3 metal oxide, for example yttrium n-propoxide.

In one embodiment, the Group 3 metal oxide or oxide of the Lanthanide or Actinide series is hydrothermally treated under conditions that include a temperature of at least 80° C., preferably at least 100° C. The hydrothermal treatment may take place in a sealed vessel at greater than atmospheric pressure. However, a preferred mode of treatment involves the use of an open vessel under reflux conditions. Agitation of the Group 3 metal oxide or the oxide of the Lanthanide or Actinide series in a liquid medium, for example, by the action of refluxing liquid and/or stirring, promotes the effective interaction of the oxide with the liquid medium. The duration of the contact of the oxide with the liquid medium is preferably at least 1 hour, preferably at least 8 hours. The liquid medium for this treatment preferably has a pH of about 6 or greater, preferably about 8 or greater. Non-limiting examples of suitable liquid media include water, hydroxide solutions (including hydroxides of $NH_4^+$, $Na^+$, $K^+$, $Mg^{2+}$, and $Ca^{2+}$), carbonate and bicarbonate solutions (including carbonates and bicarbonates of $NH_4^+$, $Na^+$, $K^+$, $Mg^{2+}$, and $Ca^{2+}$), pyridine and its derivatives, and alkyl/hydroxyl amines.

In another embodiment, the active Group 3 metal oxide or the active oxide of the Lanthanide or Actinide series is prepared by subjecting a liquid solution, such as an aqueous solution, comprising a source of ions of the metal, such as a metal salt, to conditions sufficient to cause precipitation of a hydrated precursor to the solid oxide material, such as by the addition of a precipitating reagent to the solution. Conveniently, the precipitation is conducted at a pH above 7. For example, the precipitating agent can be a base such as sodium hydroxide or ammonium hydroxide.

The temperature at which the liquid medium is maintained during the precipitation is generally less than about 200° C., such as in the range of from about 0° C. to about 200° C. A particular range of temperatures for precipitation is from about 20° C. to about 100° C. The resulting gel is preferably then hydrothermally treated at temperatures of at least 80° C., preferably at least 100° C. The hydrothermal treatment typically takes place in a vessel at atmospheric pressure. The gel, in one embodiment, is hydrothermally treated for up to 10 days, such as up to 5 days, for example up to 3 days.

The hydrated precursor to the metal oxide(s) is then recovered, for example by filtration or centrifugation, and washed and dried. The resulting material can then be calcined, such as in an oxidizing atmosphere, at a temperature of at least 400° C., such as at least 500° C., for example from about 600° C. to about 900° C., and particularly from about 650° C. to about 800° C., to form the solid oxide material. The calcination time is typically up to 48 hours, such as for about 0.5 to 24 hours, for example for about 1.0 to 10 hours. In one embodiment, calcination is carried out at about 700° C. for about 1 to about 3 hours.

Catalyst Composition

The catalyst composition of the invention includes any one of the molecular sieves previously described and one or more Group 3 metal oxides and/or one or more oxide(s) of a Lanthanide or Actinide series elements described above, optionally together with a binder and/or matrix material different from the active metal oxide(s). Typically, the weight ratio of the molecular sieve to the active metal oxide in the catalyst composition is in the range of from 5 weight percent to 800 weight percent, such as from 10 weight percent to 600 weight percent, particularly from 20 weight percent to 500 weight percent, and more particularly from 30 weight percent to 400 weight percent.

There are many different binders that are useful in forming catalyst compositions. Non-limiting examples of binders that are useful alone or in combination include various types of hydrated alumina, silicas, and/or other inorganic oxide soils. One preferred alumina containing sol is aluminum chlorhydrol. The inorganic oxide sol acts like glue binding the synthesized molecular sieves and other materials such as the matrix together, particularly after thermal treatment. Upon heating, the inorganic oxide sol, preferably having a low viscosity, is converted into an inorganic oxide binder component. For example, an alumina sol will convert to an aluminum oxide binder following heat treatment.

Aluminum chlorhydrol, a hydroxylated aluminum based sol containing a chloride counter ion, has the general formula of $Al_mO_n(OH)_oCl_p \cdot x(H_2O)$ wherein m is 1 to 20, n is 1 to 8, o is 5 to 40, p is 2 to 15, and x is 0 to 30. In one embodiment, the binder is $Al_{13}O_4(OH)_{24}Cl_7 \cdot 12(H_2O)$ as is described in G. M. Wolterman, et al., Stud. Surf. Sci. and Catal., 76, pages 105–144 (1993), which is herein incorporated by reference. In another embodiment, one or more binders are combined with one or more other non-limiting examples of alumina materials such as aluminum oxyhydroxide, γ-alumina, boehmite, diaspore, and transitional aluminas such as α-alumina, β-alumina, γ-alumina, δ-alumina, ε-alumina, κ-alumina, and ρ-alumina, aluminum trihydroxide, such as gibbsite, bayerite, nordstrandite, doyelite, and mixtures thereof.

In another embodiment, the binder is an alumina sol, predominantly comprising aluminum oxide, optionally including some silicon. In yet another embodiment, the binder is peptized alumina made by treating an alumina hydrate, such as pseudobohemite, with an acid, preferably an acid that does not contain a halogen, to prepare a sol or aluminum ion solution. Non-limiting examples of commercially available colloidal alumina soils include Nalco 8676 available from Nalco Chemical Co., Naperville, Ill., and Nyacol AL20DW available from Nyacol Nano Technologies, Inc., Ashland, Mass.

Where the catalyst composition contains a matrix material, this is preferably different from the active metal oxide and any binder. Matrix materials are typically effective in reducing overall catalyst cost, acting as thermal sinks to assist in shielding heat from the catalyst composition for example during regeneration, densifying the catalyst composition, and increasing catalyst strength such as crush strength and attrition resistance.

Non-limiting examples of matrix materials include one or more non-active metal oxides including beryllia, quartz, silica or soils, and mixtures thereof, for example silica-magnesia, silica-zirconia, silica-titania, silica-alumina and silica-alumina-thoria. In an embodiment, matrix materials are natural clays such as those from the families of montmorillonite and kaolin. These natural clays include subbentonites and those kaolins known as, for example, Dixie, McNamee, Georgia and Florida clays. Non-limiting examples of other matrix materials include haloysite, kaolinite, dickite, nacrite, or anauxite. The matrix material, such as a clay, may be subjected to well known modification processes such as calcination and/or acid treatment and/or chemical treatment.

In a preferred embodiment, the matrix material is a clay or a clay-type composition, particularly a clay or clay-type composition having a low iron or titania content, and most preferably the matrix material is kaolin. Kaolin has been found to form a pumpable, high solids content slurry, to have a low fresh surface area, and to pack together easily due to its platelet structure. A preferred average particle size of the matrix material, most preferably kaolin, is from about 0.1 $\mu$m to about 0.6 $\mu$m with a $D_{90}$ particle size distribution of less than about 1 $\mu$m.

Where the catalyst composition contains a binder or matrix material, the catalyst composition typically contains from about 1% to about 80%, such as from about 5% to about 60%, and particularly from about 5% to about 50%, by weight of the molecular sieve based on the total weight of the catalyst composition.

Where the catalyst composition contains a binder and a matrix material, the weight ratio of the binder to the matrix material is typically from 1:15 to 1:5, such as from 1:1 to 1:4, and particularly from 1:6 to 1:5. The amount of binder is typically from about 2% by weight to about 30% by weight, such as from about 5% by weight to about 20% by weight, and particularly from about 7% by weight to about 15% by weight, based on the total weight of the binder, the molecular sieve and matrix material. It has been found that a higher sieve content and lower matrix content increases the molecular sieve catalyst composition performance, whereas a lower sieve content and higher matrix content improves the attrition resistance of the composition.

The catalyst composition typically has a density in the range of from 0.5 g/cc to 5 g/cc, such as from from 0.6 g/cc to 5 g/cc, for example from 0.7 g/cc to 4 g/cc, particularly in the range of from 0.8 g/cc to 3 g/cc.

Method of Making The Catalyst Composition

In making the catalyst composition, the molecular sieve is first formed and is then physically mixed with an active Group 3 metal oxide or an active oxide of a Lanthanide or Actinide series element, preferably in a substantially dry, dried, or calcined state. Most preferably the molecular sieve and active metal oxides are physically mixed in their calcined state. Without being bound by any particular theory, it is believed that intimate mixing of the molecular sieve and one or more active metal oxides improves conversion processes using the molecular sieve composition and catalyst composition of the invention. Intimate mixing can be achieved by any method known in the art, such as mixing with a mixer muller, drum mixer, ribbon/paddle blender, kneader, or the like. Chemical reaction between the molecular sieve and the metal oxide(s) is unnecessary and, in general, is not preferred.

Where the catalyst composition contains a matrix and/or binder, the molecular sieve is conveniently initially formulated into a catalyst precursor with the matrix and/or binder and the active metal oxide is then combined with the formulated precursor. The active metal oxide can be added as unsupported particles or can be added in combination with a support, such as a binder or matrix material. The resultant catalyst composition can then be formed into useful shaped and sized particles by well-known techniques such as spray drying, pelletizing, extrusion, and the like.

In one embodiment, the molecular sieve composition and the matrix material, optionally with a binder, are combined with a liquid to form a slurry and then mixed, preferably rigorously mixed, to produce a substantially homogeneous mixture containing the molecular sieve composition. Non-limiting examples of suitable liquids include one or a combination of water, alcohol, ketones, aldehydes, and/or esters. The most preferred liquid is water. In one embodiment, the slurry is colloid-milled for a period of time sufficient to produce the desired slurry texture, sub-particle size, and/or sub-particle size distribution.

The molecular sieve composition and matrix material, and the optional binder, can be combined in the same or different liquids, and can be combined in any order, together, simultaneously, sequentially, or a combination thereof. In the preferred embodiment, the same liquid, preferably water is used. The molecular sieve composition, matrix material, and optional binder, are combined in a liquid as solids, substantially dry or in a dried form, or as slurries, together or separately. If solids are added together as dry or substantially dried solids, it is preferable to add a limited and/or controlled amount of liquid.

In one embodiment, the slurry of the molecular sieve composition, binder and matrix materials is mixed or milled to achieve a sufficiently uniform slurry of sub-particles of the molecular sieve catalyst composition that is then fed to a forming unit that produces the molecular sieve catalyst composition. In a preferred embodiment, the forming unit is spray dryer. Typically, the forming unit is maintained at a temperature sufficient to remove most of the liquid from the slurry, and from the resulting molecular sieve catalyst composition. The resulting catalyst composition when formed in this way takes the form of microspheres.

When a spray drier is used as the forming unit, typically, the slurry of the molecular sieve composition and matrix material, and optionally a binder, is co-fed to the spray drying volume with a drying gas with an average inlet temperature ranging from 200° C. to 550° C., and a combined outlet temperature ranging from 100° C. to about 225° C. In an embodiment, the average diameter of the spray dried formed catalyst composition is from about 40 $\mu$m to about 300 $\mu$m, such as from about 50 $\mu$m to about 250 $\mu$m, for example from about 50 $\mu$m to about 200 $\mu$m, and conveniently from about 65 $\mu$m to about 90 $\mu$m.

Other methods for forming a molecular sieve catalyst composition are described in U.S. patent application Ser. No. 09/617,714 filed Jul. 17, 2000 (spray drying using a recycled molecular sieve catalyst composition), now U.S. Pat. 6,509,290; which is herein incorporated by reference.

Once the molecular sieve catalyst composition is formed in a substantially dry or dried state, to further harden and/or activate the formed catalyst composition, a heat treatment such as calcination, at an elevated temperature is usually performed. Typical calcination temperatures are in the range from about 400° C. to about 1,000° C., such as from about 500° C. to about 800° C., such as from about 550° C. to about 700° C. Typical calcination environments are air (which may include a small amount of water vapor), nitrogen, helium, flue gas (combustion product lean in oxygen), or any combination thereof.

In a preferred embodiment, the catalyst composition is heated in nitrogen at a temperature of from about 600° C. to about 700° C. Heating is carried out for a period of time typically from 30 minutes to 15 hours, such as from 1 hour to about 10 hours, for example from about 1 hour to about 5 hours, and particularly from about 2 hours to about 4 hours.

Process for Using the Molecular Sieve Catalyst Compositions

The catalyst compositions described above are useful in a variety of processes including cracking, of for example a naphtha feed to light olefin(s) (U.S. Pat. No. 6,300,537) or higher molecular weight (MW) hydrocarbons to lower MW hydrocarbons; hydrocracking, of for example heavy petroleum and/or cyclic feedstock; isomerization, of for example aromatics such as xylene; polymerization, of for example one or more olefin(s) to produce a polymer product; reforming; hydrogenation; dehydrogenation; dewaxing, of for example hydrocarbons to remove straight chain paraffins; absorption, of for example alkyl aromatic compounds for separating out isomers thereof; alkylation, of for example aromatic hydrocarbons such as benzene and alkyl benzene, optionally with propylene to produce cumene or with long chain olefins; transalkylation, of for example a combination of aromatic and polyalkylaromatic hydrocarbons; dealkylation; hydrodecylization; disproportionation, of for example toluene to make benzene and paraxylene; oligomerization, of for example straight and branched chain olefin(s); and dehydrocyclization.

Preferred processes include processes for converting naphtha to highly aromatic mixtures; converting light olefin(s) to gasoline, distillates and lubricants; converting oxygenates to olefin(s); converting light paraffins to olefins and/or aromatics; and converting unsaturated hydrocarbons (ethylene and/or acetylene) to aldehydes for conversion into alcohols, acids and esters.

The most preferred process of the invention is a process directed to the conversion of a feedstock to one or more olefin(s). Typically, the feedstock contains one or more aliphatic-containing compounds such that the aliphatic moiety contains from 1 to about 50 carbon atoms, such as from 1 to 20 carbon atoms, for example from 1 to 10 carbon atoms, and particularly from 1 to 4 carbon atoms.

Non-limiting examples of aliphatic-containing compounds include alcohols such as methanol and ethanol, alkyl mercaptans such as methyl mercaptan and ethyl mercaptan, alkyl sulfides such as methyl sulfide, alkylamines such as methylamine, alkyl ethers such as dimethyl ether, diethyl ether and methylethyl ether, alkyl halides such as methyl chloride and ethyl chloride, alkyl ketones such as dimethyl ketone, formaldehydes, and various acids such as acetic acid.

In a preferred embodiment of the process of the invention, the feedstock contains one or more oxygenates, more specifically, one or more organic compound(s) containing at least one oxygen atom. In the most preferred embodiment of the process of invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts.

Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof.

In the most preferred embodiment, the feedstock is selected from one or more of methanol, ethanol, dimethyl ether, diethyl ether or a combination thereof, more preferably methanol and dimethyl ether, and most preferably methanol.

The various feedstocks discussed above, particularly a feedstock containing an oxygenate, more particularly a feedstock containing an alcohol, are converted primarily into one or more olefin(s). The olefin(s) produced from the feedstock typically have from 2 to 30 carbon atoms, preferably 2 to 8 carbon atoms, more preferably 2 to 6 carbon atoms, still more preferably 2 to 4 carbons atoms, and most preferably are ethylene and/or propylene.

The catalyst composition of the invention is particularly useful in the process that is generally referred to as the gas-to-olefins (GTO) process or alternatively, the methanol-to-olefins (MTO) process. In this process, an oxygenated feedstock, most preferably a methanol-containing feedstock, is converted in the presence of a molecular sieve catalyst composition into one or more olefin(s), preferably and predominantly, ethylene and/or propylene.

Using the catalyst composition of the invention for the conversion of a feedstock, preferably a feedstock containing one or more oxygenates, the amount of olefin(s) produced based on the total weight of hydrocarbon produced is greater than 50 weight percent, typically greater than 60 weight percent, such as greater than 70 weight percent, and preferably greater than 80 weight percent. Moreover, the amount of ethylene and/or propylene produced based on the total weight of hydrocarbon product produced is greater than 40 weight percent, typically greater than 50 weight percent, for example greater than 65 weight percent, and preferably greater than 78 weight percent. Typically, the amount ethylene produced in weight percent based on the total weight of hydrocarbon product produced, is greater than 20 weight percent, such as greater than 30 weight percent, for example greater than 40 weight percent. In addition, the amount of propylene produced in weight percent based on the total weight of hydrocarbon product produced is typically greater than 20 weight percent, such as greater than 25 weight percent, for example greater than 30 weight percent, and preferably greater than 35 weight percent.

Using the catalyst composition of the invention for the conversion of a feedstock comprising methanol and dimethylether to ethylene and propylene, it is found that the production of ethane and propane is reduced by greater than 10%, such as greater than 20%, for example greater than 30%, and particularly in the range of from about 30% to 40% compared to a similar catalyst composition at the same conversion conditions but without the active metal oxide component(s).

In addition to the oxygenate component, such as methanol, the feedstock may contains one or more diluent(s), which are generally non-reactive to the feedstock or molecular sieve catalyst composition and are typically used to reduce the concentration of the feedstock. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent, for example water, may be used either in a liquid or a vapor form, or a combination thereof. The diluent may be either added directly to the feedstock entering a reactor or added directly to the reactor, or added with the molecular sieve catalyst composition.

The present process can be conducted over a wide range of temperatures, such as in the range of from about 200° C. to about 1000° C., for example from about 250° C. to about 800° C., including from about 250° C. to about 750° C., conveniently from about 300° C. to about 650° C., typically from about 350° C. to about 600° C. and particularly from about 350° C. to about 550° C.

Similarly, the present process can be conducted over a wide range of pressures including autogenous pressure. Typically the partial pressure of the feedstock exclusive of any diluent therein employed in the process is in the range of from about 0.1 kPaa to about 5 MPaa, such as from about 5 kPaa to about 1 MPaa, and conveniently from about 20 kPaa to about 500 kPaa.

The weight hourly space velocity (WHSV), defined as the total weight of feedstock excluding any diluents per hour per weight of molecular sieve in the catalyst composition, typically ranges from about 1 $hr^{-1}$ to about 5000 $hr^{-1}$, such as from about 2 $hr^{-1}$ to about 3000 $hr^{-1}$, for example from about 5 $hr^{-1}$ to about 1500 $hr^{-1}$, and conveniently from about 10 $hr^{-1}$ to about 1000 $hr^{-1}$. In one embodiment, the WHSV is greater than 20 $hr^{-1}$ and, where feedstock contains methanol and/or dimethyl ether, is in the range of from about 20 $hr^{-1}$ to about 300 $hr^{-1}$.

Where the process is conducted in a fluidized bed, the superficial gas velocity (SGV) of the feedstock including diluent and reaction products within the reactor system, and particularly within a riser reactor(s), is at least 0.1 meter per second (m/sec), such as greater than 0.5 m/sec, such as greater than 1 m/sec, for example greater than 2 m/sec, conveniently greater than 3 m/sec, and typically greater than 4 m/sec. See for example U.S. patent application Ser. No. 09/708,753 filed Nov. 8, 2000, which is herein incorporated by reference.

The process of the invention is conveniently conducted as a fixed bed process, or more typically as a fluidized bed process (including a turbulent bed process), such as a continuous fluidized bed process, and particularly a continuous high velocity fluidized bed process.

The process can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described in for example U.S. Pat. Nos. 4,076,796, 6,287,522 (dual riser), and *Fluidization Engineering*, D. Kunii and O. Levenspiel, Robert E. Krieger Publishing Company, New York, N.Y. 1977, which are all herein fully incorporated by reference.

The preferred reactor types are riser reactors generally described in *Riser Reactor, Fluidization and Fluid-Particle Systems*, pages 48 to 59, F. A. Zenz and D. F. Othmo, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), now U.S. Published Pat. Appl. No. 2005-0152814; which are all herein fully incorporated by reference.

In one practical embodiment, the process is conducted as a fluidized bed process or high velocity fluidized bed process utilizing a reactor system, a regeneration system and a recovery system.

In such a process the reactor system would conveniently include a fluid bed reactor system having a first reaction zone within one or more riser reactor(s) and a second reaction zone within at least one disengaging vessel, typically comprising one or more cyclones. In one embodiment, the one or more riser reactor(s) and disengaging vessel are contained within a single reactor vessel. Fresh feedstock, preferably containing one or more oxygenates, optionally with one or more diluent(s), is fed to the one or more riser reactor(s) into which a molecular sieve catalyst composition or coked version thereof is introduced. In one embodiment, prior to being introduced to the riser reactor(s), the molecular sieve catalyst composition or coked version thereof is contacted with a liquid, preferably water or methanol, and/or a gas, for example, an inert gas such as nitrogen.

In an embodiment, the amount of fresh feedstock fed as a liquid and/or a vapor to the reactor system is in the range of from 0.1 weight percent to about 85 weight percent, such as from about 1 weight percent to about 75 weight percent, more typically from about 5 weight percent to about 65 weight percent based on the total weight of the feedstock including any diluent contained therein. The liquid and vapor feedstocks may be the same composition, or may contain varying proportions of the same or different feedstocks with the same or different diluents.

The feedstock entering the reactor system is preferably converted, partially or fully, in the first reactor zone into a gaseous effluent that enters the disengaging vessel along with the coked catalyst composition. In the preferred embodiment, cyclone(s) are provided within the disengaging vessel to separate the coked catalyst composition from the gaseous effluent containing one or more olefin(s) within the disengaging vessel. Although cyclones are preferred, gravity effects within the disengaging vessel can also be used to separate the catalyst composition from the gaseous effluent. Other methods for separating the catalyst composition from the gaseous effluent include the use of plates, caps, elbows, and the like.

In one embodiment, the disengaging vessel includes a stripping zone, typically in a lower portion of the disengaging vessel. In the stripping zone the coked catalyst composition is contacted with a gas, preferably one or a combination of steam, methane, carbon dioxide, carbon monoxide, hydrogen, or an inert gas such as argon, preferably steam, to recover adsorbed hydrocarbons from the coked catalyst composition that is then introduced to the regeneration system.

The coked catalyst composition is withdrawn from the disengaging vessel and introduced to the regeneration system. The regeneration system comprises a regenerator where the coked catalyst composition is contacted with a regeneration medium, preferably a gas containing oxygen, under conventional regeneration conditions of temperature, pressure and residence time.

Non-limiting examples of suitable regeneration media include one or more of oxygen, $O_3$, $SO_3$, $N_2O$, NO, $NO_2$, $N_2O_5$, air, air diluted with nitrogen or carbon dioxide, oxygen and water (U.S. Pat. No. 6,245,703), carbon monoxide and/or hydrogen. Suitable regeneration conditions are those capable of burning coke from the coked catalyst composition, preferably to a level less than 0.5 weight percent based on the total weight of the coked molecular sieve catalyst composition entering the regeneration system. For example, the regeneration temperature may be in the range of from about 200° C. to about 1500° C., such as from about 300° C. to about 1000° C., for example from about 450° C. to about 750° C., and conveniently from about 550°

C. to 700° C. The regeneration pressure may be in the range of from about 15 psia (103 kPaa) to about 500 psia (3448 kPaa), such as from about 20 psia (138 kPaa) to about 250 psia (1724 kPaa), including from about 25 psia (172 kPaa) to about 150 psia (1034 kPaa), and conveniently from about 30 psia (207 kPaa) to about 60 psia (414 kPaa).

The residence time of the catalyst composition in the regenerator may be in the range of from about one minute to several hours, such as from about one minute to 100 minutes, and the volume of oxygen in the regeneration gas may be in the range of from about 0.01 mole percent to about 5 mole percent based on the total volume of the gas.

The burning of coke in the regeneration step is an exothermic reaction, and in an embodiment, the temperature within the regeneration system is controlled by various techniques in the art including feeding a cooled gas to the regenerator vessel, operated either in a batch, continuous, or semi-continuous mode, or a combination thereof. A preferred technique involves withdrawing the regenerated catalyst composition from the regeneration system and passing it through a catalyst cooler to form a cooled regenerated catalyst composition. The catalyst cooler, in an embodiment, is a heat exchanger that is located either internal or external to the regeneration system. Other methods for operating a regeneration system are disclosed in U.S. Pat. No. 6,290,916 (controlling moisture), which is herein fully incorporated by reference.

The regenerated catalyst composition withdrawn from the regeneration system, preferably from a catalyst cooler, is combined with a fresh molecular sieve catalyst composition and/or re-circulated molecular sieve catalyst composition and/or feedstock and/or fresh gas or liquids, and returned to the riser reactor(s). In one embodiment, the regenerated catalyst composition withdrawn from the regeneration system is returned to the riser reactor(s) directly, preferably after passing through a catalyst cooler. A carrier, such as an inert gas, feedstock vapor, steam or the like, may be used, semi-continuously or continuously, to facilitate the introduction of the regenerated catalyst composition to the reactor system, preferably to the one or more riser reactor(s).

By controlling the flow of the regenerated catalyst composition or cooled regenerated catalyst composition from the regeneration system to the reactor system, the optimum level of coke on the molecular sieve catalyst composition entering the reactor is maintained. There are many techniques for controlling the flow of a catalyst composition described in Michael Louge, *Experimental Techniques, Circulating Fluidized Beds*, Grace, Avidan and Knowlton, eds., Blackie, 1997 (336–337), which is herein incorporated by reference.

Coke levels on the catalyst composition are measured by withdrawing the catalyst composition from the conversion process and determining its carbon content. Typical levels of coke on the molecular sieve catalyst composition, after regeneration, are in the range of from 0.01 weight percent to about 15 weight percent, such as from about 0.1 weight percent to about 10 weight percent, for example from about 0.2 weight percent to about 5 weight percent, and conveniently from about 0.3 weight percent to about 2 weight percent based on the weight of the molecular sieve.

The gaseous effluent is withdrawn from the disengaging system and is passed through a recovery system. There are many well known recovery systems, techniques and sequences that are useful in separating olefin(s) and purifying olefin(s) from the gaseous effluent. Recovery systems generally comprise one or more or a combination of various separation, fractionation and/or distillation towers, columns, splitters, or trains, reaction systems such as ethylbenzene manufacture (U.S. Pat. No. 5,476,978) and other derivative processes such as aldehydes, ketones and ester manufacture (U.S. Pat. No. 5,675,041), and other associated equipment, for example various condensers, heat exchangers, refrigeration systems or chill trains, compressors, knock-out drums or pots, pumps, and the like.

Non-limiting examples of these towers, columns, splitters or trains used alone or in combination include one or more of a demethanizer, preferably a high temperature demethanizer, a de-ethanizer, a depropanizer, a wash tower often referred to as a caustic wash tower and/or quench tower, absorbers, adsorbers, membranes, ethylene (C2) splitter, propylene (C3) splitter, butene (C4) splitter, and the like.

Various recovery systems useful for recovering predominantly olefin(s), preferably light olefin(s) such as ethylene, propylene and/or butene, are described in U.S. Pat. No. 5,960,643 (secondary rich ethylene stream), U.S. Pat. Nos. 5,019,143, 5,452,581 and 5,082,481 (membrane separations), U.S. Pat. 5,672,197 (pressure dependent adsorbents), U.S. Pat. No. 6,069,288 (hydrogen removal), U.S. Pat. No. 5,904,880 (recovered methanol to hydrogen and carbon dioxide in one step), U.S. Pat. No. 5,927,063 (recovered methanol to gas turbine power plant), and U.S. Pat. No. 6,121,504 (direct product quench), U.S. Pat. No. 6,121,503 (high purity olefins without superfractionation), and U.S. Pat. No. 6,293,998 (pressure swing adsorption), which are all herein fully incorporated by reference.

Other recovery systems that include purification systems, for example for the purification of olefin(s), are described in *Kirk-Othmer Encyclopedia of Chemical Technology*, 4th Edition, Volume 9, John Wiley & Sons, 1996, pages 249–271 and 894–899, which is herein incorporated by reference. Purification systems are also described in for example, U.S. Pat. No. 6,271,428 (purification of a diolefin hydrocarbon stream), U.S. Pat. No. 6,293,999 (separating propylene from propane), and U.S. patent application Ser. No. 09/689,363 filed Oct. 20, 2000 (purge stream using hydrating catalyst), now U.S. Pat. 6,593,506; which are herein incorporated by reference.

Generally accompanying most recovery systems is the production, generation or accumulation of additional products, by-products and/or contaminants along with the preferred prime products. The preferred prime products, the light olefins, such as ethylene and propylene, are typically purified for use in derivative manufacturing processes such as polymerization processes. Therefore, in the most preferred embodiment of the recovery system, the recovery system also includes a purification system. For example, the light olefin(s) produced particularly in a MTO process are passed through a purification system that removes low levels of by-products or contaminants.

Non-limiting examples of contaminants and by-products include generally polar compounds such as water, alcohols, carboxylic acids, ethers, carbon oxides, sulfur compounds such as hydrogen sulfide, carbonyl sulfides and mercaptans, ammonia and other nitrogen compounds, arsine, phosphine and chlorides. Other contaminants or by-products include hydrogen and hydrocarbons such as acetylene, methyl acetylene, propadiene, butadiene and butyne.

Typically, in converting one or more oxygenates to olefin(s) having 2 or 3 carbon atoms, a minor amount hydrocarbons, particularly olefin(s), having 4 or more carbon atoms is also produced. The amount of $C_4+$ hydrocarbons is normally less than 20 weight percent, such as less than 10 weight percent, for example less than 5 weight percent, and particularly less than 2 weight percent, based on the total weight of the effluent gas withdrawn from the process, excluding water. Typically, therefore the recovery system may include one or more reaction systems for converting the $C_{4}+$ impurities to useful products.

Non-limiting examples of such reaction systems are described in U.S. Pat. No. 5,955,640 (converting a four carbon product into butene-1), U.S. Pat. No. 4,774,375 (isobutane and butene-2 oligomerized to an alkylate gasoline), U.S. Pat. No. 6,049,017 (dimerization of n-butylene), U.S. Pat. Nos. 4,287,369 and 5,763,678 (carbonylation or hydroformulation of higher olefins with carbon dioxide and hydrogen making carbonyl compounds), U.S. Pat. No. 4,542,252 (multistage adiabatic process), U.S. Pat. No. 5,634,354 (olefin-hydrogen recovery), and Cosyns, J. et al., *Process for Upgrading C3, C4and C5Olefinic Streams*, Pet. & Coal, Vol. 37, No. 4 (1995) (dimerizing or oligomerizing propylene, butylene and pentylene), which are all herein fully incorporated by reference.

The preferred light olefin(s) produced by any one of the processes described above are high purity prime olefin(s) products that contain a single carbon number olefin in an amount greater than 80 percent, such as greater than 90 weight percent, such as greater than 95 weight percent, for example at least about 99 weight percent, based on the total weight of the olefin.

In one practical embodiment, the process of the invention forms part of an integrated process for producing light olefin(s) from a hydrocarbon feedstock, preferably a gaseous hydrocarbon feedstock, particularly methane and/or ethane. The first step in the process is passing the gaseous feedstock, preferably in combination with a water stream, to a syngas production zone to produce a synthesis gas (syngas) stream, typically comprising carbon dioxide, carbon monoxide and hydrogen. Syngas production is well known, and typical syngas temperatures are in the range of from about 700° C. to about 1200° C. and syngas pressures are in the range of from about 2 MPa to about 100 MPa. Synthesis gas streams are produced from natural gas, petroleum liquids, and carbonaceous materials such as coal, recycled plastic, municipal waste or any other organic material. Preferably synthesis gas stream is produced via steam reforming of natural gas.

The next step in the process involves contacting the synthesis gas stream generally with a heterogeneous catalyst, typically a copper based catalyst, to produce an oxygenate containing stream, often in combination with water. In one embodiment, the contacting step is conducted at temperature in the range of from about 150° C. to about 450° C. and a pressure in the range of from about 5 MPa to about 10 MPa.

This oxygenate containing stream, or crude methanol, typically contains the alcohol product and various other components such as ethers, particularly dimethyl ether, ketones, aldehydes, dissolved gases such as hydrogen methane, carbon oxide and nitrogen, and fuel oil. The oxygenate containing stream, crude methanol, can then be passed through one or more well known purification processes, such as distillation, separation and fractionation, resulting in a purified oxygenate containing stream, for example, commercial Grade A and AA methanol.

The oxygenate containing stream or purified oxygenate containing stream, optionally with one or more diluents, can then be used as a feedstock in a process to produce light olefin(s), such as ethylene and/or propylene. Non-limiting examples of this integrated process are described in EP-B-0 933 345, which is herein fully incorporated by reference.

In another more fully integrated process, that optionally is combined with the integrated processes described above, the olefin(s) produced are directed to, in one embodiment, one or more polymerization processes for producing various polyolefins. (See for example U.S. patent application Ser. No. 09/615,376 filed Jul. 13, 2000, which is herein fully incorporated by reference.)

Polymerization processes include solution, gas phase, slurry phase and a high pressure processes, or a combination thereof. Particularly preferred is a gas phase or a slurry phase polymerization of one or more olefin(s) at least one of which is ethylene or propylene. These polymerization processes utilize a polymerization catalyst that can include any one or a combination of the molecular sieve catalysts discussed above, however, the preferred polymerization catalysts are the Ziegler-Natta, Phillips-type, metallocene, metallocene-type and advanced polymerization catalysts, and mixtures thereof.

In a preferred embodiment, the integrated process comprises a process for polymerizing one or more olefin(s) in the presence of a polymerization catalyst system in a polymerization reactor to produce one or more polymer products, wherein the one or more olefin(s) have been made by converting an alcohol, particularly methanol, using a molecular sieve catalyst composition as described above. The preferred polymerization process is a gas phase polymerization process and at least one of the olefins(s) is either ethylene or propylene, and preferably the polymerization catalyst system is a supported metallocene catalyst system. In this embodiment, the supported metallocene catalyst system comprises a support, a metallocene or metallocene-type compound and an activator. Preferably the activator is a non-coordinating anion or alumoxane, or combination thereof, and most preferably the activator is alumoxane.

The polymers produced by the polymerization processes described above include linear low density polyethylene, elastomers, plastomers, high density polyethylene, low density polyethylene, polypropylene and polypropylene copolymers. The propylene based polymers produced by the polymerization processes include atactic polypropylene, isotactic polypropylene, syndiotactic polypropylene, and propylene random, block or impact copolymers.

EXAMPLES

In order to provide a better understanding of the present invention including representative advantages thereof, the following Examples are offered.

In the Examples, LEI is defined as the ratio of the lifetime of a molecular sieve catalyst composition containing an active metal oxide(s) compared to that of the same molecular sieve in the absence of a metal oxide, defined as having an LEI of 1. For the purpose of determining LEI, lifetime is defined as the cumulative amount of oxygenate converted, preferably into one or more olefin(s), per gram of molecular sieve, until the conversion rate drops to about 10% of its initial value. If the conversion has not fallen to 10% of its initial value by the end of the experiment, lifetime is estimated by linear extrapolation based on the rate of decrease in conversion over the last two data points in the experiment. For the purposes of determining the LEI for the following Examples in a preferred oxygenate conversion process, methanol is converted to one or more olefin(s) at 475° C., 25 psig (172 kPag) and a methanol weight hourly space velocity of 100 $h^{-1}$.

"Prime Olefin" is the sum of the selectivity to ethylene and propylene. The ratio "$C_2^=/C_3^=$" is the ratio of the ethylene to propylene selectivity weighted over the run. The "$C_3$ Purity" is calculated by dividing the propylene selectivity by the sum of the propylene and propane selectivities.

The selectivities for methane, ethylene, ethane, propylene, propane, $C_4$'s and $C_5+$'s are average selectivities weighted over the run. Note that the $C_5+$'s consist only of $C_5$'s, $C_6$'s and $C_7$'s. The selectivity values do not sum to 100% in the Tables because they have been corrected for coke as is well known.

Example A
Preparation of Molecular Sieve

A silicoaluminophosphate molecular sieve, SAPO-34, designated as MSA, was crystallized in the presence of tetraethyl ammonium hydroxide (R1) and dipropylamine (R2) as the organic structure directing agents or templating agents. A mixture of the following mole ratio composition:

0.2 $SiO_2/Al_2O_3/P_2O_5$/0.9 R1/1.5 R2/50 $H_2O$.

was prepared by initially mixing an amount of Condea Pural SB with deionised water, to form a slurry. To this slurry was added an amount of phosphoric acid (85%). These additions were made with stirring to form a homogeneous mixture. To this homogeneous mixture Ludox AS40 (40% of $SiO_2$) was added, followed by the addition of R1 with mixing to form a homogeneous mixture. To this homogeneous mixture R2 was added. This homogeneous mixture was then crystallized with agitation in a stainless steel autoclave by heating to 170° C. for 40 hours. This provided a slurry of the crystalline molecular sieve. The crystals were then separated from the mother liquor by filtration. The molecular sieve crystals were then mixed with a binder and matrix material and formed into particles by spray drying.

Example B
Conversion Process

All catalytic or conversion data presented was obtained using a microflow reactor consisting of a stainless steel reactor (¼ inch (0.64 cm) outer diameter) located in a furnace to which vaporized methanol was fed. The reactor was maintained at a temperature of 475° C. and a pressure of 25 psig (172.4 kPag) The flow rate of the methanol was such that the flow rate of methanol on weight basis per gram of molecular sieve, also known as the weight hourly space velocity (WHSV) was 100 $h^{-1}$. Product gases exiting the reactor were collected and analyzed using gas chromatography. The catalyst load in each experiment was 50 mg and the reactor bed was diluted with quartz to minimize hot spots in the reactor. In particular, for the catalyst composition of the invention, a physical mixture of the MSA molecular sieve of Example A and the active metal oxide(s) was used. The total catalyst composition load remained 50 mg, and the methanol flow rate was adjusted as the amount of molecular sieve in the reactor bed was reduced by the addition of the mixed metal oxide such that the methanol WHSV was 100 $h^{-1}$ based on the amount of molecular sieve in the reactor bed.

Example 1

A sample of $La(NO_3)_3 \cdot xH_2O$ (Aldrich Chemical Company) was calcined in air at 700° C. for 3 hours to produce lanthanum oxide.

Example 2

Fifty grams of $La(NO_3)_3 \cdot xH_2O$ (Aldrich Chemical Company) were dissolved with stirring in 500 ml of distilled water. The pH was adjusted to 9 by the addition of concentrated ammonium hydroxide. This slurry was then put in polypropylene bottles and placed in a steambox (100° C.) for 72 hours. The product formed was recovered by filtration, washed with excess water, and dried overnight at 85° C. A portion of this catalyst was calcined to 600° C. in flowing air for 3 hours to produce lanthanum oxide ($La_2O_3$).

Example 3

Fifty grams of $La(NO_3)_3 \cdot 6H_2O$ were dissolved with stirring in 500 ml of distilled water. The pH was adjusted to 9 by the addition of concentrated ammonium hydroxide. This slurry was then put in polypropylene bottles and placed in a steambox (100° C.) for 72 hours. The product formed was recovered by filtration, washed with excess water, and dried overnight at 85° C. A portion of this catalyst was calcined to 600° C. in flowing air for 3 hours to produce yttrium oxide ($Y_2O_3$).

Example 4

A sample of $Sc(NO_3)_3 \cdot xH_2O$ (Aldrich Chemical Company) was calcined in air at 700° C. for 3 hours to produce scandium oxide ($Sc_2O_3$).

Example 5

Fifty grams of $Ce(NO_3)_3 \cdot 6H_2O$ were dissolved with stirring in 500 ml of distilled water. The pH was adjusted to 8 by the addition of concentrated ammonium hydroxide. This slurry was then put in polypropylene bottles and placed in a steambox (100° C.) for 72 hours. The product formed was recovered by filtration, washed with excess water, and dried overnight at 85° C. A portion of this catalyst was calcined to 600° C. in flowing air for 3 hours to produce cerium oxide ($Ce_2O_3$).

Example 6

Fifty grams of $Pr(NO_3)_3 \cdot 6H_2O$ were dissolved with stirring in 500 ml of distilled water. The pH was adjusted to 8 by the addition of concentrated ammonium hydroxide. This slurry was then put in polypropylene bottles and placed in a steambox (100° C.) for 72 hours. The product formed was recovered by filtration, washed with excess water, and dried overnight at 85° C. A portion of this catalyst was calcined to 600° C. in flowing air for 3 hours to produce praseodymium oxide ($Pr_2O_3$).

Example 7

Fifty grams of $Nd(NO_3)_3 \cdot 6H_2O$ were dissolved with stirring in 500 ml of distilled water. The pH was adjusted to 9 by the addition of concentrated ammonium hydroxide. This slurry was then put in polypropylene bottles and placed in a steambox (100° C.) for 72 hours. The product formed was recovered by filtration, washed with excess water, and dried overnight at 85° C. A portion of this catalyst was calcined to 600° C. in flowing air for 3 hours to produce neodymium oxide ($Nd_2O_3$).

Example 8

Thirty nine grams of $Ce(NO_3)_3 \cdot 6H_2O$ and 7.0 grams of $La(NO_3)_3 \cdot 6H_2O$ were dissolved with stirring in 500 ml of distilled water. Another solution containing 20 grams of concentrated ammonium hydroxide and 500 ml of distilled water was prepared. These two solutions were combined at the rate of 50 ml/min using a nozzle mixer. The pH of the final composite was adjusted to approximately 9 by the addition of concentrated ammonium hydroxide. This slurry was then put in polypropylene bottles and placed in a steambox (100° C.) for 72 hours. The product formed was recovered by filtration, washed with excess water, and dried overnight at 85° C. A portion of this catalyst was calcined to 700° C. in flowing air for 3 hours to produce a mixed metal oxide containing a nominal 5 weight percent lanthanum based on the final weight of the mixed metal oxide.

Example 9

Nine grams of $Ce(NO_3)_3 \cdot 6H_2O$ and 30.0 grams of $La(NO_3)_3 \cdot 6H_2O$ were dissolved with stirring in 500 ml of distilled water. Another solution containing 20 grams of concentrated ammonium hydroxide and 500 ml of distilled water was prepared. These two solutions were combined at the rate of 50 ml/min using a nozzle mixer. The pH of the final composite was adjusted to approximately 9 by the addition of concentrated ammonium hydroxide. This slurry was then put in polypropylene bottles and placed in a steambox (100° C.) for 72 hours. The product formed was recovered by filtration, washed with excess water, and dried overnight at 85° C. A portion of this catalyst was calcined to 700° C. in flowing air for 3 hours to produce a mixed metal oxide containing a nominal 5 weight percent cerium based on the final weight of the mixed metal oxide.

Example 10

The carbon dioxide uptake of the oxides of Examples 1 through 9 were measured using a Mettler TGA/SDTA 851 thermogravimetric analysis system under ambient pressure. The metal oxide samples were first dehydrated in flowing air to about 500° C. for one hour after which the uptake of carbon dioxide was measured at 100° C. The surface area of the samples were measured in accordance with the method of Brunauer, Emmett, and Teller (BET) to provide the oxide uptake in terms of mg carbon dioxide/$m^2$ of the metal oxide in Table 1.

TABLE 1

| Example | Catalyst Dry Weight (mg) | $CO_2$ Adsorbed (mg) | Surface Area ($m^2$/g) | $CO_2$ Uptake (mg/$m^2$) |
|---|---|---|---|---|
| 1 | 22 | 0.1846 | 40 | 0.210 |
| 2 | 31 | 0.6487 | 38 | 0.551 |
| 3 | 24 | 0.3296 | 80 | 0.172 |
| 4 | 20 | 0.0490 | 33 | 0.074 |
| 5 | 143 | 0.7714 | 57 | 0.095 |
| 6 | 50 | 0.3136 | 24 | 0.261 |
| 7 | 41 | 0.6491 | 18 | 0.880 |
| 8 | 130 | 0.8407 | 51 | 0.127 |
| 9 | 42 | 1.2542 | 46 | 0.649 |

Comparative Example 11

In this Comparative Example 11 (CEx. 11) the molecular sieve catalyst composition produced in Example A was tested in the process of Example B using 50 mg of the molecular sieve catalyst composition without an active metal oxide. The results of the run are presented in Table 2 and Table 3.

Example 12

In this Example, the molecular sieve catalyst composition produced in Example A was tested in the process of Example B using 40 mg of the molecular sieve catalyst composition with 10 mg of $La_2O_3$ produced via nitrate decomposition in Example 1. The components were well mixed and then diluted with sand to form the reactor bed. The results of this experiment are shown in Tables 2 and 3 illustrating that the addition of $La_2O_3$, an active Group 3 metal oxide, increased lifetime by 149%. Selectivity to ethane decreased by 36% and selectivity to propane decreased by 32%, suggesting a significant reduction in hydrogen transfer reactions.

Example 13

In this Example, the molecular sieve catalyst composition produced in Example A was tested in the process of Example B using 40 mg of the molecular sieve catalyst composition with 10 mg of $La_2O_3$ produced via precipitation in Example 2. The components were well mixed and then diluted with sand to form the reactor bed. The results of this experiment are shown in Tables 2 and 3 illustrating that the addition of $La_2O_3$ produced via precipitation, an active Group 3 metal oxide, increased lifetime by 340%. Selectivity to ethane decreased by 55% and selectivity to propane decreased by 44%, suggesting a significant reduction in hydrogen transfer reactions.

Example 14

In this Example 14, the molecular sieve catalyst composition produced in Example A was tested in the process of Example B using 40 mg of the molecular sieve catalyst composition with 10 mg of $Y_2O_3$ produced in Example 3. The components were well mixed and then diluted with sand to form the reactor bed. The results of this experiment are shown in Tables 2 and 3 illustrating that the addition of $Y_2O_3$, an active Group 3 metal oxide, increased lifetime by 1090%. Selectivity to ethane decreased by 45% and selectivity to propane decreased by 28%, suggesting a significant reduction in hydrogen transfer reactions.

Example 15

In this Example 15, the molecular sieve catalyst composition produced in Example A was tested in the process of Example B using 40 mg of the molecular sieve catalyst composition with 10 mg of $Sc_2O_3$ produced in Example 4. The components were well mixed and then diluted with sand to form the reactor bed. The results of this experiment are shown in Tables 2 and 3 illustrating that the addition of $Sc_2O_3$, an active Group 3 metal oxide, increased lifetime by 167%. Selectivity to ethane decreased by 27% and selectivity to propane decreased by 21%, suggesting a significant reduction in hydrogen transfer reactions.

Example 16

In this Example 16, the molecular sieve catalyst composition produced in Example A was tested in the process of Example B using 40 mg of the molecular sieve catalyst composition with 10 mg of $Ce_2O_3$ produced in Example 5. The components were well mixed and then diluted with sand to form the reactor bed. The results of this experiment are shown in Tables 2 and 3 illustrating that the addition of $Ce_2O_3$, an active Lanthanide metal oxide, increased lifetime by 630%. Selectivity to ethane decreased by 50% and selectivity to propane decreased by 34%, suggesting a significant reduction in hydrogen transfer reactions.

Example 17

In this Example 17, the molecular sieve catalyst composition produced in Example A was tested in the process of Example B using 40 mg of the molecular sieve catalyst composition with 10 mg of $Pr_2O_3$ produced in Example 6. The components were well mixed and then diluted with sand to form the reactor bed. The results of this experiment are shown in Tables 2 and 3 illustrating that the addition of $Pr_2O_3$, an active Lanthanide metal oxide, increased lifetime by 640%. Selectivity to ethane decreased by 51% and selectivity to propane decreased by 38%, suggesting a significant reduction in hydrogen transfer reactions.

Example 18

In this Example 18, the molecular sieve catalyst composition produced in Example A was tested in the process of Example B using 40 mg of the molecular sieve catalyst composition with 10 mg of $Nd_2O_3$ produced in Example 7. The components were well mixed and then diluted with sand to form the reactor bed. The results of this experiment are shown in Tables 2 and 3 illustrating that the addition of $Nd_2O_3$, an active Lanthanide metal oxide, increased lifetime by 340%. Selectivity to ethane decreased by 49% and selectivity to propane decreased by 34%, suggesting a significant reduction in hydrogen transfer reactions.

Example 19

In this Example 19, the molecular sieve catalyst composition produced in Example A was tested in the process of Example B using 40 mg of the molecular sieve catalyst composition with 10 mg of the mixed metal oxide produced in Example 8. The components were well mixed and then diluted with sand to form the reactor bed. The results of this experiment are shown in Tables 2 and 3 illustrating that the addition of 5% $LaO_x/Ce_2O_3$, an active Lanthanide metal oxide modified by a Group 3 oxide, increased lifetime by 450%. Selectivity to ethane decreased by 47% and selectivity to propane decreased by 37%, suggesting a significant reduction in hydrogen transfer reactions.

Example 20

In this Example 20, the molecular sieve catalyst composition produced in Example A was tested in the process of Example B using 40 mg of the molecular sieve catalyst composition with 10 mg of the mixed metal oxide produced in Example 9. The components were well mixed and then diluted with sand to form the reactor bed. The results of this experiment are shown in Tables 2 and 3 illustrating that the addition of 5% $CeO_x/La_2O_3$, an active Group 3 metal oxide modified by a Lanthanide series oxide, increased lifetime by 260%. Selectivity to ethane decreased by 56% and selectivity to propane decreased by 45%, suggesting a significant reduction in hydrogen transfer reactions.

TABLE 2

| Example | Reactor Bed Composition | Lifetime Extension Index (LEI) | Prime Olefin (%) | $C_2=/C_3=$ | $C_3$ Purity (%) |
|---|---|---|---|---|---|
| CEx.11 | 100% MSA | 1.0 | 72.99 | 0.90 | 94.1 |
| 12 | 80% MSA/20% $La_2O_3$ | 2.5 | 73.84 | 0.81 | 96.1 |
| 13 | 80% MSA/20% $La_2O_3$ | 4.4 | 73.78 | 0.74 | 96.9 |
| 14 | 80% MSA/20% $Y_2O_3$ | 11.9 | 73.68 | 0.76 | 96.0 |
| 15 | 80% MSA/20% $Sc_2O_3$ | 2.7 | 73.74 | 0.81 | 95.5 |
| 16 | 80% MSA/20% $Ce_2O_3$ | 7.3 | 70.51 | 0.69 | 96.3 |
| 17 | 80% MSA/20% $Pr_2O_3$ | 7.4 | 72.37 | 0.72 | 96.6 |
| 18 | 80% MSA/20% $Nd_2O_3$ | 4.4 | 72.57 | 0.71 | 96.3 |
| 19 | 80% MSA/20% $LaO_x/Ce_2O_3$ | 5.5 | 70.64 | 0.73 | 96.4 |
| 20 | 80% MSA/20% $CeO_x/La_2O_3$ | 3.6 | 70.52 | 0.71 | 96.9 |

TABLE 3

| Example | Reactor Bed Composition | $CH_4$ | $C_2=$ | $C_2o$ | $C_3=$ | $C_3o$ | $C_4$'s | $C_5+$ |
|---|---|---|---|---|---|---|---|---|
| CEx.11 | 100% MSA | 2.04 | 34.50 | 0.78 | 38.49 | 2.43 | 14.01 | 3.82 |
| 12 | 80% MSA/20% $La_2O_3$ | 1.61 | 33.05 | 0.50 | 40.79 | 1.65 | 14.96 | 4.51 |
| 13 | 80% MSA/20% $La_2O_3$ | 1.38 | 31.43 | 0.35 | 42.35 | 1.37 | 15.03 | 5.51 |
| 14 | 80% MSA/20% $Y_2O_3$ | 1.39 | 31.85 | 0.43 | 41.83 | 1.74 | 14.43 | 5.61 |
| 15 | 80% MSA/20% $Sc_2O_3$ | 1.67 | 33.08 | 0.57 | 40.66 | 1.93 | 14.49 | 4.45 |
| 16 | 80% MSA/20% $Ce_2O_3$ | 2.05 | 28.89 | 0.39 | 41.62 | 1.61 | 15.29 | 6.83 |
| 17 | 80% MSA/20% $Pr_2O_3$ | 1.59 | 30.18 | 0.38 | 42.19 | 1.51 | 15.22 | 6.06 |
| 18 | 80% MSA/20% $Nd_2O_3$ | 1.64 | 30.2 | 0.40 | 42.37 | 1.61 | 15.13 | 5.68 |
| 19 | 80% MSA/20% $LaO_x/Ce_2O_3$ | 2.62 | 29.85 | 0.41 | 40.80 | 1.52 | 14.07 | 7.14 |
| 20 | 80% MSA/20% $CeO_x/La_2O_3$ | 2.13 | 29.16 | 0.34 | 41.36 | 1.34 | 14.86 | 7.92 |

While the present invention has been described and illustrated by reference to particular embodiments, those of ordinary skill in the art will appreciate that the invention lends itself to variations not necessarily illustrated herein. For example, it is contemplated that a plug flow, fixed bed or fluidized bed process are used in combination, particularly in different reaction zones within a single or multiple reactor system. It is also contemplated the molecular sieve compositions described herein are useful as absorbents, adsorbents, gas separators, detergents, water purifiers, and for other various uses such as agriculture and horticulture. It is within the scope of this invention to add one or more active Group 3 metal oxide(s) to the synthesis mixture for making a molecular sieve as described above. Also, it is contemplated that one or more molecular sieves are used in the catalyst composition. For this reason, then, reference should be made solely to the appended claims for purposes of determining the true scope of the present invention.

We claim:

1. A catalyst composition comprising a molecular sieve physically mixed with at least one oxide of a metal selected from Group 3 of the Periodic Table of Elements, the Lanthanide series of elements and the Actinide series of elements, wherein said metal oxide has an uptake of carbon dioxide at 100° C. of at least 0.03 mg/m² of the metal oxide.

2. The catalyst composition of claim 1 wherein said metal oxide has an uptake of carbon dioxide at 100° C. of at least 0.04 mg/m² of the metal oxide.

3. The catalyst composition of claim 1 wherein said metal oxide has an uptake of carbon dioxide at 100° C. of less than 10 mg/m² of the metal oxide.

4. The catalyst composition of claim 1 wherein said metal oxide has an uptake of carbon dioxide at 100° C. of less than 5 mg/m² of the metal oxide.

5. The catalyst composition of claim 1 and also including at least one of a binder and a matrix material different from said metal oxide.

6. The catalyst composition of claim 1 and also including a binder and a matrix material each being different from one another and from said metal oxide.

7. The catalyst composition of claim 6 wherein the binder is an alumina sol and the matrix material is a clay.

8. The catalyst composition of claim 1 wherein said metal oxide is selected from lanthanum oxide, yttrium oxide, scandium oxide, cerium oxide, praseodymium oxide, neodymium oxide, samarium oxide, thorium oxide and mixtures thereof.

9. The catalyst composition of claim 1 wherein said metal oxide is yttrium oxide.

10. The catalyst composition of claim 1 wherein the molecular sieve comprises a framework including at least two tetrahedral units selected from [SiO$_4$], [AlO$_4$] and [PO$_4$] units.

11. The catalyst composition of claim 10 wherein the molecular sieve comprises a silicoaluminophosphate.

12. The catalyst composition of claim 10 wherein the molecular sieve comprises a CHA framework-type molecular sieve.

13. The catalyst composition of claim 12 wherein the molecular sieve further comprises an AEI framework-type molecular sieve.

14. The catalyst composition of claim 1 wherein the weight ratio of the molecular sieve to metal oxide is in the range of from 5 percent to 800 percent.

15. A molecular sieve catalyst composition comprising a Group 3 metal oxide and/or an oxide of the Lanthanide or Actinide series elements, a binder, a matrix material, and a silicoaluminophosphate molecular sieve, said oxide(s) being physically mixed with said molecular sieve.

16. A method for making a catalyst composition, the method comprising physically mixing first particles comprising a molecular sieve with second particles comprising at least one oxide of a metal selected from Group 3 of the Periodic Table of Elements, the Lanthanide series of elements and the Actinide series of elements, wherein said metal oxide has an uptake of carbon dioxide at 100° C. of at least 0.03 mg/m$^2$ of the metal oxide particles.

17. The method of claim 16 wherein at least one said first and said second particles also include at least one of a binder and a matrix material.

18. The method of claim 16 wherein said first particles comprise silicoaluminophosphate molecular sieve and/or an aluminophosphate molecular sieve.

19. The method of claim 17 wherein said first particles comprise a silicoaluminophosphate molecular sieve, a binder including an alumina sol and a matrix material including a clay.

20. The method of claim 16 wherein said metal oxide is lanthanum oxide, yttrium oxide cerium oxide or a mixture thereof.

21. A method of making a catalyst composition, the method comprising:
  (i) synthesizing a molecular sieve from a reaction mixture comprising at least one templating agent and at least two of a silicon source, a phosphorus source and an aluminum source; and
  (ii) recovering the molecular sieve synthesized in (i);
  (iii) forming a hydrated precursor of an oxide of a metal selected from Group 3 of the Periodic Table of Elements, the Lanthanide series of elements and the Actinide series of elements by precipitation from a solution containing a source of ions of said metal;
  (iv) recovering the hydrated precursor formed in (iii);
  (v) calcining the hydrated precursor recovered in (iv) to form a calcined metal oxide that has an uptake of carbon dioxide at 100° C. of at least 0.03 mg/m$^2$ of the metal oxide; and
  (vi) physically mixing the molecular sieve recovered in (i) and the calcined metal oxide produced in (v).

22. The method of claim 21 wherein the molecular sieve and/or the metal oxide is combined with a binder and/or a matrix material prior to (vi).

23. The method of claim 21 wherein the weight ratio of the molecular sieve to the calcined metal oxide is in the range of from 30 percent to 400 percent.

24. The method of claim 21 wherein the molecular sieve is spray dried with a matrix material and a binder prior to (vi).

25. The method of claim 24 wherein the molecular sieve is a silicoaluminophosphate, the binder is an alumina sol, and the matrix material is a clay.

26. The method of claim 21 wherein the metal oxide is selected from lanthanum oxide, yttrium oxide, scandium oxide, cerium oxide, praseodymium oxide, neodymium oxide and mixtures thereof.

27. The method of claim 21 wherein said precipitation is conducted at a pH above 7.

28. The method of claim 21 wherein (iii) also includes hydrothermally treating the precipitate at a temperature of at least 80° C. for up to 10 days.

29. The method of claim 21 wherein (v) is conducted at a temperature in the range of from about 400° C. to about 900° C.

* * * * *